United States Patent
Chen et al.

(10) Patent No.: US 12,239,674 B2
(45) Date of Patent: Mar. 4, 2025

(54) LACTOBACILLUS RHAMNOSUS LRH05 ISOLATE, AND COMPOSITION INCLUDING THE SAME AND USE THEREOF

(71) Applicant: SYNBIO TECH INC., Kaohsiung (TW)

(72) Inventors: Yung-Tsung Chen, New Taipei (TW); Jin-Seng Lin, Tainan (TW)

(73) Assignee: SYNBIO TECH INC., Kaohsiung (TW)

( * ) Notice: Subject to any disclaimer, the term of this patent is extended or adjusted under 35 U.S.C. 154(b) by 356 days.

(21) Appl. No.: 17/604,960

(22) PCT Filed: Jun. 17, 2021

(86) PCT No.: PCT/IB2021/055352
§ 371 (c)(1),
(2) Date: Oct. 19, 2021

(87) PCT Pub. No.: WO2022/162439
PCT Pub. Date: Aug. 4, 2022

(65) Prior Publication Data
US 2023/0107022 A1    Apr. 6, 2023

(30) Foreign Application Priority Data

Jan. 27, 2021 (TW) .................. 110103124

(51) Int. Cl.
| | |
|---|---|
| *A61K 35/747* | (2015.01) |
| *A61K 9/00* | (2006.01) |
| *A61P 1/00* | (2006.01) |
| *A61P 3/00* | (2006.01) |
| *A61P 3/04* | (2006.01) |
| *A61P 3/06* | (2006.01) |
| *A61P 3/10* | (2006.01) |

(52) U.S. Cl.
CPC .......... *A61K 35/747* (2013.01); *A61K 9/0053* (2013.01); *A61P 1/00* (2018.01); *A61P 3/00* (2018.01); *A61P 3/04* (2018.01); *A61P 3/06* (2018.01); *A61P 3/10* (2018.01); *A23V 2002/00* (2013.01); *A23V 2400/175* (2023.08)

(58) Field of Classification Search
None
See application file for complete search history.

(56) References Cited

FOREIGN PATENT DOCUMENTS

| | | |
|---|---|---|
| CN | 110468070 A | 11/2019 |
| WO | 2010130785 A2 | 11/2010 |
| WO | 2020198808 A1 | 10/2020 |

OTHER PUBLICATIONS

Sun et al., "Lactobacillus rhamnosus LRa05 improves lipid accumulation in mice fed with a high fat diet via regulating the intestinal microbiota, reducing glucose content and promoting liver carbohydrate", Food and Function, vol. 11, pp. 9514-9525. (Year: 2020).*
Galicia-Garcia et al., "Pathophysiology of Type 2 Diabetes Mellitus", International Journal of Molecular Sciences, vol. 21(17), Article 6275, pp. 1-34. (Year: 2020).*
International Search Report for International Application No. PCT/IB2021/055352 Dated Oct. 27, 2021, 7 pages.

* cited by examiner

*Primary Examiner* — Michelle F. Paguio Frising
*Assistant Examiner* — Grant C Currens
(74) *Attorney, Agent, or Firm* — MH2 Technology Law Group, LLP

(57) ABSTRACT

Disclosed herein is an isolated strain of *Lactobacillus rhamnosus* LRH05, which is deposited at Deutsche Sammlung von Mikroorganismen und Zellkulturen GmbH under an accession number DSM 33616. Also disclosed herein are a composition including the isolated strain of *Lactobacillus rhamnosus* LRH05 for treating a metabolic syndrome-related disorder and for modifying gut microbiota, and use of the isolated strain of *Lactobacillus rhamnosus* LRH05 for treating a metabolic syndrome-related disorder and for modifying gut microbiota.

3 Claims, 17 Drawing Sheets

Specification includes a Sequence Listing.

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Forward primer 27F' for PCR amplification of
      bacterial 16S rDNA fragment

<400> SEQUENCE: 1
agagtttgat cctggctcag                                                  20

<210> SEQ ID NO 2
<211> LENGTH: 18
<212> TYPE: DNA
<213> ORGANISM: Artificial Sequence
<220> FEATURE:
<223> OTHER INFORMATION: Reverse primer 1492R' for PCR amplification of
      bacterial 16S rDNA fragment

<400> SEQUENCE: 2
ggttaccttg ttacgact                                                    18

<210> SEQ ID NO 3
<211> LENGTH: 1188
<212> TYPE: DNA
<213> ORGANISM: Lactobacillus rhamnosus
<220> FEATURE:
<223> OTHER INFORMATION: 16S rDNA sequence of Lactobacillus rhamnosus
      LRH05

<400> SEQUENCE: 3
gtgtagccca ggtcataagg ggcatgatga tttgacgtca tccccacctt cctccggttt      60
gtcaccggca gtcttactag agtgcccaac taaatgctgg caactagtca taagggttgc     120
gctcgttgcg ggacttaacc caacatctca cgacacgagc tgacgacaac catgcaccac     180
ctgtcatttt gcccccgaag gggaaacctg atctctcagg tgatcaaaag atgtcaagac     240
ctggtaaggt tcttcgcgtt gcttcgaatt aaaccacatg ctccaccgct tgtgcgggcc     300
cccgtcaatt cctttgagtt tcaaccttgc ggtcgtactc cccaggcgga atgcttaatg     360
```

```
cgttagctgc ggcactgaag ggcggaaacc ctccaacacc tagcattcat cgtttacggc    420
atggactacc agggtatcta atcctgttcg ctacccatgc tttcgagcct cagcgtcagt    480
tacagaccag acagccgcct tcgccactgg tgttcttcca tatatctacg catttcaccg    540
ctacacatgg agttccactg tcctcttctg cactcaagtt tcccagtttc cgatgcactt    600
cctcggttaa gccgagggct ttcacatcag acttaaaaaa ccgcctgcgc tcgctttacg    660
cccaataaat ccgataacg cttgccacct acgtattacc gcggctgctg gcacgtagtt    720
agccgtggct ttctggttgg ataccgtcac gccgacaaca gttactctgc gaccattct    780 tctccaacaa cagagtttta cgacccgaaa gccttcttca ctcacgcggc gttgctccat    840
cagacttgcg tccattgtgg aagattccct actgctgcct cccgtaggag tttgggccgt    900
gtctcagtcc caatgtggcc gatcaacctc tcagttcggc tacgtatcat tgccttggtg    960
agccgttacc tcaccaacta gctaatacgc cgcgggtcca tccaaaagcg atagcttacg   1020
ccatctttca gccaagaacc atgcggttct tggatttatg cggtattagc atctgtttcc   1080
aaatgttatc ccccacttaa gggcaggtta cccacgtgtt actcacccgt ccgccactcg   1140
ttcaaaatta aatcaagatg caagcacctt tcaataatca gaactcgt                1188
```

```
<210> SEQ ID NO 4
<211> LENGTH: 50
<212> TYPE: DNA
<213> ORGANISM: Artificial Sequence
<220> FEATURE:
<223> OTHER INFORMATION: Forward primer for PCR amplification of
      bacterial 16S rDNA fragment
<220> FEATURE:
<221> NAME/KEY: misc_feature
<222> LOCATION: (42)..(42)
<223> OTHER INFORMATION: n is a or g or c or t/u
<220> FEATURE:
<221> NAME/KEY: misc_feature
<222> LOCATION: (46)..(46)
<223> OTHER INFORMATION: w is a or t/u

<400> SEQUENCE: 4
tcgtcggcag cgtcagatgt gtataagaga cagcctacgg gnggcwgcag               50

<210> SEQ ID NO 5
<211> LENGTH: 55
<212> TYPE: DNA
<213> ORGANISM: Artificial Sequence
<220> FEATURE:
<223> OTHER INFORMATION: Reverse primer for PCR amplification of
      bacterial 16S rDNA fragment
<220> FEATURE:
<221> NAME/KEY: misc_feature
<222> LOCATION: (41)..(41)
<223> OTHER INFORMATION: h is a or c or t/u
<220> FEATURE:
<221> NAME/KEY: misc_feature
<222> LOCATION: (42)..(42)
<223> OTHER INFORMATION: v is a or g or c

<400> SEQUENCE: 5
gtctcgtggg ctcggagatg tgtataagag acaggactac hvgggtatct aatcc         55
```

LACTOBACILLUS RHAMNOSUS LRH05 ISOLATE, AND COMPOSITION INCLUDING THE SAME AND USE THEREOF

CROSS-REFERENCE TO RELATED APPLICATIONS

This application is a national phase entry of International Application No. PCT/IB2021/055352 filed on 17 Jun. 2021, which claims priority to Taiwanese Invention patent application No. 110103124 filed on 27 Jan. 2021. The entire content of each of the aforementioned patent applications is incorporated herein by reference.

SEQUENCE LISTING

The instant application contains a Sequence Listing which has been submitted electronically in ASCII format and is hereby incorporated by reference in its entirety. Said ASCII copy, created on 5-12-2022, is named 0307_0005_SL and is 4 kilobytes 3,336 bytes in size.

FIELD

The present disclosure relates to an isolated strain of *Lactobacillus rhamnosus* LRH05, which has been deposited at Deutsche Sammlung von Mikroorganismen und Zellkulturen GmbH under an accession number DSM 33616. The present disclosure also relates to a composition including the isolated strain of *Lactobacillus rhamnosus* LRH05, and use of the isolated strain of *Lactobacillus rhamnosus* LRH05 for treating a metabolic syndrome-related disorder and for modifying gut microbiota.

BACKGROUND

Metabolic syndrome is a complex condition associated with an increased risk of developing cardiovascular diseases and type 2 diabetes. The symptoms, features and complications of the metabolic syndrome include at least three of the following: type 2 diabetes mellitus (T2DM), insulin resistance, hypertension, central obesity, high cholesterol, combined hyperlipidemia (which includes elevated low-density lipoprotein (LDL), decreased high-density lipoprotein (HDL), and elevated triglycerides), and fatty liver (especially in concurrent obesity).

Several prevention and treatment strategies, such as diet and nutrition management, and use of anti-obesity drugs, hypoglycemic drugs, and hypolipidemic drugs, have been taken to combat metabolic syndrome. However, these drugs might not be able to achieve the desired therapeutic effect and might also cause severe side effects.

Probiotics are resident normal flora of the intestinal tract and believed to play important roles in regulating proper intestinal immunity and digestion by balancing intestinal microflora. These beneficial microorganisms are widely used as live microbial dietary supplements and can help restoring intestinal microfloral balance. Many species of lactic acid bacteria (LAB) are conferred with the generally recognized as safe (GRAS) status, and are widely used as probiotics. Common LAB include *Lactobacillus* spp., *Lactococcus* spp., *Pediococcus* spp., *Streptococcus* spp., *Enterococcus* spp., *Bifidobacterium* spp., *Bacillus* spp., *Leuconostoc* spp., etc. LAB have been shown to be capable of inhibiting the growth of pathogenic bacteria in the gastrointestinal tract and alleviating lactose intolerance, and to have anti-cancer, anti-bacterial, anti-fatigue, and blood pressure lowering effects.

Previous studies demonstrated that certain strains of LAB are effective in losing weight, promoting glucose and fat metabolism, and ameliorating insulin resistance. For example, it has been reported in K. Mazloom et al. (2019), Nutrients, 11(2):258 that *Lactobacillus rhamnosus* GG (LGG) can effectively attenuate weight gain, reduce lipid accumulation, and improve insulin sensitivity in mice fed with a high fat diet.

In spite of the aforesaid, there is still a need to screen a new species and/or a strain of LAB that can exhibit satisfactory efficacy in treating a metabolic syndrome-related disorder.

SUMMARY

Therefore, in a first aspect, the present disclosure provides an isolated strain of *Lactobacillus rhamnosus* LRH05 which can alleviate at least one of the drawbacks of the prior art.

The isolated strain of *Lactobacillus rhamnosus* LRH05 is deposited at Deutsche Sammlung von Mikroorganismen und Zellkulturen GmbH under an accession number DSM 33616.

In a second aspect, the present disclosure provides a composition for treating a metabolic syndrome-related disorder, which can alleviate at least one of the drawbacks of the prior art, and which includes the aforesaid isolated strain of *Lactobacillus rhamnosus* LRH05.

In a third aspect, the present disclosure provides a method for treating a metabolic syndrome-related disorder, which can alleviate at least one of the drawbacks of the prior art, and which includes administering to a subject in need thereof a pharmaceutical composition containing the abovementioned isolated strain of *Lactobacillus rhamnosus* LRH05.

In a fourth aspect, the present disclosure provides use of the aforesaid isolated strain of *Lactobacillus rhamnosus* LRH05 in the manufacture of a medicament for treating a metabolic syndrome-related disorder in a subject. Such use can alleviate at least one of the drawbacks of the prior art.

In a fifth aspect, the present disclosure provides the aforesaid isolated strain of *Lactobacillus rhamnosus* LRH05 for use in the treatment of a metabolic syndrome-related disorder in a subject. Such strain can alleviate at least one of the drawbacks of the prior art.

In a sixth aspect, the present disclosure provides a composition for modifying gut microbiota, which can alleviate at least one of the drawbacks of the prior art, and which includes the aforesaid isolated strain of *Lactobacillus rhamnosus* LRH05.

In a seventh aspect, the present disclosure provides a method for modifying gut microbiota, which can alleviate at least one of the drawbacks of the prior art, and which includes administering to a subject in need thereof a composition containing the abovementioned isolated strain of *Lactobacillus rhamnosus* LRH05.

In an eighth aspect, the present disclosure provides use of the aforesaid isolated strain of *Lactobacillus rhamnosus* LRH05 in the manufacture of a composition for modifying gut microbiota in a subject. Such use can alleviate at least one of the drawbacks of the prior art.

In a ninth aspect, the present disclosure provides the aforesaid isolated strain of *Lactobacillus rhamnosus* LRH05 for use in modifying gut microbiota in a subject. Such strain can alleviate at least one of the drawbacks of the prior art.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
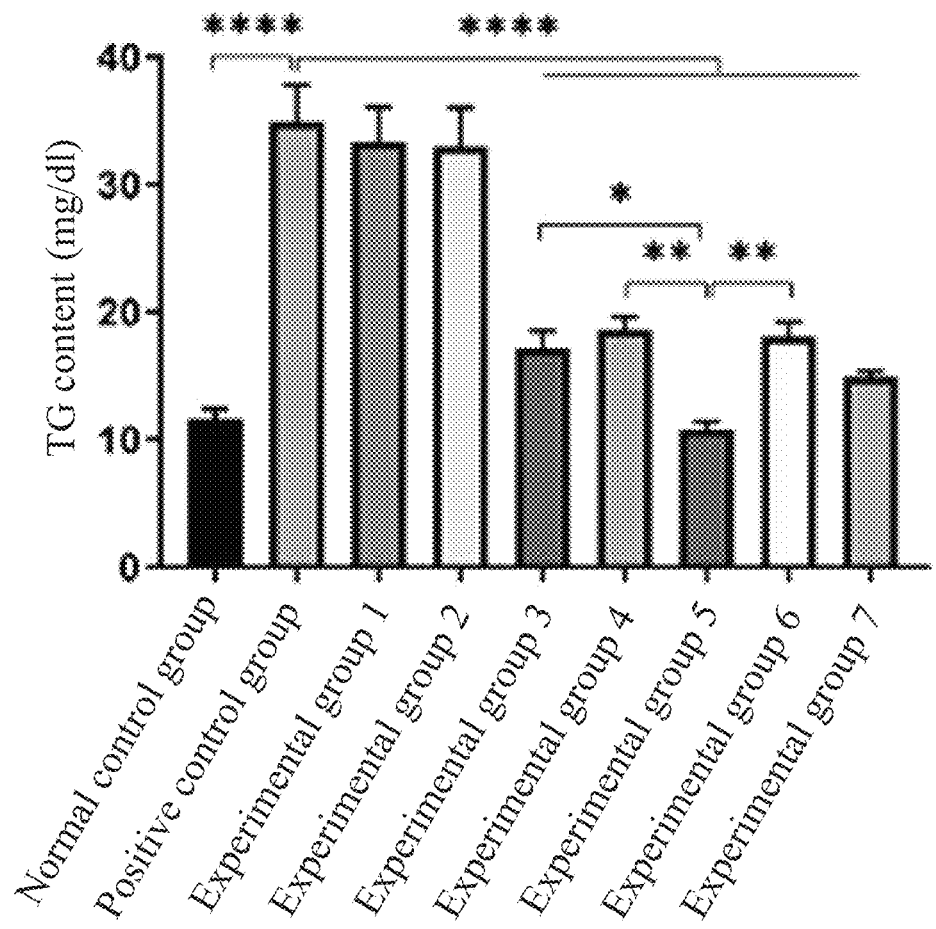
FIG. 1 shows the triglyceride (TG) content in each group of Example 1, infra, in which the symbol "*" represents $p<0.05$ (compared with the experimental group 5), the symbol "" represents $p<0.01$ (compared with the experimental group 5), and the symbol "*" represents $p<0.0001$ (compared with the positive **control group)

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

By virtue of research, the applicant surprisingly found that a new strain of *Lactobacillus rhamnosus* LRH05 is capable of inhibiting the absorption of fat by intestinal epithelial cells, and reducing the body weight, blood lipids, and body fat in a subject with metabolic syndrome. In addition, the anti-diabetic activity of *Lactobacillus rhamnosus* LRH05 is significantly higher than that of *Lactobacillus rhamnosus* GG (LGG).

Therefore, the present disclosure provides an isolated strain of *Lactobacillus rhamnosus* LRH05, which has been deposited at the Biosource Collection and Research Center (BCRC) of the Food Industry Research and Development Institute (FIRDI), Taiwan under an accession number BCRC 911013 since Jul. 31, 2020, and which has also been deposited at the Deutsche Sammlung von Mikroorganismen und Zellkulturen (DSMZ) GmbH under an accession number DSM 33616 since Aug. 10, 2020 in accordance with the Budapest Treaty.

According to the present disclosure, the isolated strain of *Lactobacillus rhamnosus* LRH05 may be live cells or dead cells, concentrated or non-concentrated, a liquid, a paste, a semi-solid, a solid (e.g., a pellet, a granule, or a powder), and may be heat-inactivated, frozen, dried, or freeze-dried (e.g., may be in freeze-dried form or spray/fluid bed dried form). In an exemplary embodiment, the isolated strain of *Lactobacillus rhamnosus* LRH05 is in a liquid form.

The present disclosure also provides a composition for treating a metabolic syndrome-related disorder, which includes the aforesaid isolated strain of *Lactobacillus rhamnosus* LRH05.

In certain embodiments, the composition of the present disclosure may be formulated as a food product using a standard technique well known to one of ordinary skill in the art. For example, the composition may be directly added to an edible material or may be used to prepare an intermediate composition (e.g., a premix) suitable to be subsequently added to the edible material.

As used herein, the term "food product" refers to any article or substance that can be ingested by a subject into the body thereof. Examples of the food product may include, but are not limited to, fluid milk products (e.g., milk and concentrated milk), fermented milk (e.g., yogurt, sour milk, and frozen yogurt), milk powder, ice cream, cream cheese, dry cheese, soybean milk, fermented soybean milk, vegetable fruit juice, fruit juice, sport drinks, confectionery, jelly, candies, health foods, animal feeds, and dietary supplements.

In certain embodiments, the composition of the present disclosure may be formulated as a pharmaceutical composition. The pharmaceutical composition may further include a pharmaceutically acceptable carrier, and may be made into a dosage form suitable for oral administration using technology well-known to those skilled in the art. Examples of the oral dosage form include, but are not limited to, sterile powder, tablets, troches, lozenges, pellets, capsules, dispersible powder, granule, solutions, suspensions, emulsions, drops, syrup, elixirs, slurry, and the like.

Examples of the pharmaceutically acceptable carrier may include, but are not limited to, solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the pharmaceutically acceptable carrier are within the expertise of those skilled in the art.

The present disclosure provides a method for treating a metabolic syndrome-related disorder, which includes administering to a subject in need thereof a pharmaceutical composition containing the aforesaid isolated strain of *Lactobacillus rhamnosus* LRH05.

The present disclosure also provides use of the aforesaid isolated strain of *Lactobacillus rhamnosus* LRH05 in the manufacture of a medicament for treating a metabolic syndrome-related disorder in a subject. In certain embodiments, the medicament is in a dosage form for oral administration.

Moreover, the present disclosure provides the aforesaid isolated strain of *Lactobacillus rhamnosus* LRH05 for use in the treatment of a metabolic syndrome-related disorder in a subject.

As used herein, the term "treating" or "treatment" means preventing, reducing, alleviating, ameliorating, relieving, or controlling one or more clinical signs of a disease or disorder, and lowering, stopping or reversing the progression of the severity of the condition(s) or symptom(s) that is being treated.

As used herein, the term "administering" or "administration" means introducing, providing or delivering a predetermined active ingredient to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

According to the present disclosure, examples of the metabolic syndrome-related disorder may include, but are not limited to, obesity, hypertension, dyslipidemia (such as hyperlipidemia, hypertriglyceridemia, hypercholesterolemia, and hyperlipoproteinemia), insulin resistance or diabetes mellitus (such as type 2 diabetes mellitus (T2DM)), atherosclerosis, cardiovascular diseases (CVDs) (such as coronary artery diseases (CADs), acute myocardial infarction, stroke, heart failure, cardiac arrhythmias, and hypertensive heart diseases), and fatty liver diseases (also known as hepatic steatosis) (such as acute fatty liver, chronic fatty liver, macrovesicular fatty liver, microvesicular fatty liver, and non-alcoholic fatty liver diseases (NAFLD)).

The dose and frequency of administration of the composition of the present disclosure may vary depending on the following factors: the severity of the illness or disorder to be treated, routes of administration, and age, physical condition and response of the subject to be treated. In general, the composition may be administered in a single dose or in several doses.

Furthermore, the aforesaid isolated strain of *Lactobacillus rhamnosus* LRH05 has been proven to be effective in modifying gut microbiota. As such, it is contemplated that the composition provided in this disclosure can be used for modifying gut microbiota.

Therefore, the present disclosure further provides a method for modifying gut microbiota, which includes administering to a subject in need thereof the composition described above.

In certain embodiments, the composition for modifying gut microbiota is a pharmaceutical composition. The administration route, dosage and pharmaceutically acceptable carrier of this pharmaceutical composition are similar to those described above for the pharmaceutical composition for treating a metabolic syndrome-related disorder. In other embodiments, the composition for modifying gut microbiota is a food product as described above.

The present disclosure also provides use of the aforesaid isolated strain of *Lactobacillus rhamnosus* LRH05 in the manufacture of a composition for modifying gut microbiota in a subject as described above. In certain embodiments, the composition is a pharmaceutical composition in a dosage form for oral administration as described above. In other embodiments, the composition is a food product as described above.

Moreover, the present disclosure provides the aforesaid isolated strain of *Lactobacillus rhamnosus* LRH05 for use in modifying gut microbiota in a subject.

The present disclosure will be further described by way of the following examples. However, it should be understood that the following examples are intended solely for the purpose of illustration and should not be construed as limiting the present disclosure in practice.

EXAMPLES

General Experimental Materials:
1. Source and Cultivation of Mouse Embryonic Fibroblast Cell Line 3T3-L1

Mouse embryonic fibroblast cell line 3T3-L1 (ATCC® CRL-173™) was purchased from American Type Culture Collection (ATCC, Manassas, Va., USA). The 3T3-L1 cells were grown in a 10-cm Petri dish containing Dulbecco's Modified Eagle's Medium (DMEM) (Cat. No. D6429, Sigma-Aldrich) supplemented with 10% newborn calf serum (NCS) (Cat. No. 16010159, Gibco), 1.5 g/L sodium bicarbonate, 100 U/mL penicillin, 100 µg/mL streptomycin, and 0.25 µg/mL penicillin-streptomycin-amphotericin B (Cat. No. 03-033-1B, Biological Industries). The 3T3-L1 cells were cultivated in an incubator with culture conditions set at 37° C. and 5% $CO_2$. Medium change was performed every two to three days. Cell passage was performed when the cultured cells reached about 70% of confluence.

2. Experimental Mice

Male C57BL/6 mice (8 weeks old, with a body weight of approximately 22 g) used in the following experiments were purchased from BioLasco Taiwan Co., Ltd. All the experimental mice were housed in an animal room under the following laboratory conditions: an alternating 12-hour light and 12-hour dark cycle, a temperature maintained at 22° C.±2° C., and a relative humidity maintained at 40% to 60%. Furthermore, water and feed were provided ad libitum for all the experimental mice. All experimental procedures involving the experimental mice were in compliance with the legal provision of the Animal Protection Act of Taiwan, and were carried out according to the guidelines of the Animal Care Committee of the Council of Agriculture, Taiwan.

General Procedures:
1. Statistical Analysis

All the experiments described below were performed in triplicate. The experimental data are expressed as mean±standard deviation (SD). Statistical analysis was conducted using GraphPad Prism 7.0 (GraphPad Software, San Diego, USA). All the data were analyzed using one-way analysis of variance (ANOVA) followed by Tukey's post hoc test or Dunnett's post hoc test, so as to evaluate the differences between the groups.

Statistical significance is indicated by $p<0.05$.

Example 1. Preliminary Screening of *Lactobacillus* Isolates Having Anti-Adipogenic Activity Experimental Materials and Procedures:
A. Source and Isolation of Tested Strains Seven *Lactobacillus* isolates, i.e. LA25, LA27, LRH09, LRH10, LRH69, LRH05, and LR47, were obtained through screening using Difco Lactobacilli MRS (De Man, Rogosa and Sharpe) Agar. A respective one of the seven *Lactobacillus* isolates was inoculated into MRS broth, and was then cultured at 30° C. for 16 hours.

Thereafter, a suitable amount of a glycerol solution was added into the respective resultant culture to reach a final concentration of 20% (v/v). The resultant bacterial solutions were stored at −80° C. for subsequent use.
B. Screening of *Lactobacillus* Isolates Able to Inhibit Differentiation of 3T3-L1 Cells to Adipocytes 0.1 mL of a respective one of the seven bacterial solutions prepared in section A of this example was inoculated into 10 mL of MRS broth, and was then cultured at 37° C. for 16 hours. The aforesaid inoculation and cultivaton steps were repeated twice. 0.1 mL of a respective one of the resultant cultures was inoculated into 10 mL of MRS broth, and was then cultured at 37° C. for 18 hours. After centrifugation at 3,000 rpm and 4° C. for 10 minutes, the resultant cell pellet was collected, followed by suspending in a 0.85% sodium chloride solution, so as to obtain a bacterial suspension having a bacterial concentration of $10^{10}$ CFU/mL. Each of the bacterial suspensions was placed on ice, and was homogenized using a XL-2000 Microson ultrasonic homogenizer (Misonix Inc). After centrifugation at 12,000 rpm and 4° C. for 10 minutes, the cell-free intracellular extract was collected.

The cell-free intracellular extracts were subjected to analysis of 3T3-L1 cell differentiation generally according to the method described in Katja Zebisch et al. (2012), *Anal. Biochem.*, (1):88-90. Briefly, the 3T3-L1 cells were divided into 9 groups, including one normal control group, one positive control group, and seven experimental groups (i.e., experimental groups 1 to 7). Each group of the 3T3-L1 cells was incubated in a respective well of a 24-well culture plate containing 1 mL of basal medium (i.e., DMEM-high glucose (Cat. No. D6429, Sigma-Aldrich) supplemented with 10% NCS and 100 U/mL penicillin-streptomycin-amphotericin B) at $1\times10^4$ cells/well, followed by cultivation in an incubator (37° C., 5% $CO_2$) for 4 days.

Afterwards, for the positive control group and the seven experimental groups, the medium in each well was replaced with 1 mL of differentiation medium I (i.e., basal medium supplemented with 1 μg/mL insulin, 0.5 mM 3-isobutyl-1-methylxanthine (IBMX), and 0.25 μM dexamethasone), followed by cultivation in an incubator (37° C., 5% $CO_2$) for 3 days. Subsequently, the medium in each well was replaced with 1 mL of differentiation medium II (i.e., basal medium supplemented with 1 μg/mL insulin), followed by cultivation in an incubator (37° C., 51 $CO_2$) for 3 days, so as to induce 3T3-L1 cell differentiation into adipocytes.

During the 6-day experimental period above, each of the cell cultures of the seven experimental groups was treated with the respective cell-free intracellular extract (10 μL/day)
as shown in Table 1, and the cell culture of the positive control group was treated with a 0.85% sodium chloride solution (10 μL/day).

In addition, during the 6-day experimental period above, for the normal control group, the medium in each well was replaced with 1 mL of fresh basal medium every two days, and the cell culture of the normal control group received no treatment.

TABLE 1

| Group | Treating agent |
|---|---|
| Normal control group | — |
| Positive control group | 0.85% sodium chloride solution |
| Experimental group 1 | The cell-free intracellular extract from *Lactobacillus* isolate LA25 |
| Experimental group 2 | The cell-free intracellular extract from *Lactobacillus* isolate LA27 |
| Experimental group 3 | The cell-free intracellular extract from *Lactobacillus* isolate LRH69 |
| Experimental group 4 | The cell-free intracellular extract from *Lactobacillus* isolate LRH10 |
| Experimental group 5 | The cell-free intracellular extract from *Lactobacillus* isolate LRH05 |
| Experimental group 6 | The cell-free intracellular extract from *Lactobacillus* isolate LRH09 |
| Experimental group 7 | The cell-free intracellular extract from *Lactobacillus* isolate LR47 |

Afterwards, the cell culture of each group was subjected to determination of triglyceride (TG) content using a triglyceride colorimetric assay kit (Cat. No. 10010303, Cayman, USA) in accordance with the manufacturer's instructions. The data thus obtained were analyzed according to the method described in section 1 of "General Procedures".

Referring to FIG. 1, the TG contents determined in the experimental groups 3 to 7 were each lower than those determined in the experimental groups 1 to 2 and the positive control group. Particularly, the TG content regarding the experimental group 5 was significantly lower than those regarding the experimental groups 3 to 4 and 6, indicating that *Lactobacillus* isolate LRH05 has the best ability to inhibit the differentiation of 3T3-L1 cells to adipocytes.

Therefore, *Lactobacillus* isolate LRH05 showed more potential for development, and was subjected to characteristic analysis described below.

Example 2. Characteristic Analysis of *Lactobacillus* Isolate LRH05

In order to identify the bacterial species of *Lactobacillus* isolate LRH05, the following 16S rDNA sequence analysis and determination of carbohydrate fermentation profiling were conducted.

A. 16S rDNA Sequence Analysis

Genomic DNA of the *Lactobacillus* isolate LRH05 was extracted using Genomic DNA Mini Kit (Geneaid Biotech Ltd., Cat. No. GB100/GB300). The thus obtained genomic DNA was used as a template and was subjected to polymerase chain reaction (PCR) that was performed using a designed primer pair specific for 16S ribosomal DNA (rDNA) and the reaction conditions shown in Table 2, thereby obtaining a PCR product having a size of approximately 1,188 bp.

TABLE 2

| Contents | | Volume (µL) |
|---|---|---|
| Genomic DNA of *Lactobacillus* isolate LRH05 (50-100 ng) | | 1 |
| 16S rDNA-specific primer pair | Forward primer 27F' (10 µM): 5'-agagtttgatcctggctcag-3' (SEQ ID No: 1) | 0.5 |
| | Reverse primer 1492R' (10 µM): 5'-ggttaccttgttacgact-3' (SEQ ID No: 2) | 0.5 |
| Fast-Run ™ 2X Taq Master Mix (Protect, Cat. No. SA-TMM228) | | 10 |
| ddH$_2$O | | 8 |

Operation conditions:
denaturation at 95° C. for 5 min, followed by 30 cycles of the following reactions: denaturation at 95° C. for 60 sec, primer annealing at 50° C. for 60 sec, and extension at 72° C. for 60 sec; and lastly, elongation at 72° C. for 8 min.

The resultant PCR product was subjected to 2% agarose gel electrophoresis analysis for molecular weight verification.

Thereafter, the PCR product was verified by sequencing analysis which was entrusted to Genomics BioSci & Tech Co., Ltd., Taiwan, so as to obtain the 16S rDNA sequence (SEQ ID No: 3) of *Lactobacillus* isolate LRH05. Through comparison with the data in the NCBI's gene database, it was found that the 16S rDNA sequence of *Lactobacillus* isolate LRH05 has 99.9% identity to a part of the 16S rDNA sequence (GenBank accession number: KF 554252.1) of *Lactobacillus rhamnosus* strain g26.

In view of the aforesaid experimental results, *Lactobacillus* isolate LRH05 of the present disclosure is identified as *Lactobacillus rhamnosus*. In order to confirm whether *Lactobacillus rhamnosus* strain LRH05 (i.e. *Lactobacillus* isolate LRH05) is a novel *Lactobacillus rhamnosus* strain, the following experiment was conducted.

B. Carbohydrate Fermentation Profiling

The carbohydrate fermentation profile of *Lactobacillus rhamnosus* strain LRH05 was determined using API® 50 CH microbial identification kit (bioMerieux). The result is shown in Table 3 below.

TABLE 3

| Carbohydrate | Capability of fermenting carbohydrate tested to produce acid |
|---|---|
| Glycerol | − |
| Erythritol | − |
| D-Arabinose | − |
| L-Arabinose | − |
| D-Ribose | + |
| D-Xylose | − |
| L-Xylose | − |
| D-Adonitol | − |
| Methyl-β-D-xylopyranoside | − |
| D-Galactose | − |
| D-Glucose | + |

TABLE 3-continued

| Carbohydrate | Capability of fermenting carbohydrate tested to produce acid |
|---|---|
| D-Fructose | + |
| D-Mannose | + |
| L-Sorbose | + |
| L-Rhamnose | / |
| Dulcitol | − |
| Inositol | − |
| D-Mannitol | + |
| D-Sorbitol | / |
| Methyl-α-D-mannopyranoside | − |
| Methyl-α-D-glucopyranoside | / |
| N-Acetylglucosamine | + |
| Amygdalin | + |
| Arbutin | + |
| Esculin | + |
| Salicin | + |
| D-Cellobiose | + |
| D-Maltose | − |
| D-Lactose | + |
| D-Melibiose | − |
| D-Saccharose | − |
| D-Trehalose | + |
| Inulin | − |
| D-Melezitose | + |
| D-Raffinose | − |
| Amidon | − |
| Glycogen | − |
| Xylitol | − |
| Gentiobiose | / |
| D-Turanose | + |
| D-Lyxose | − |
| D-Tagatose | + |
| D-Fucose | − |
| L-Fucose | − |
| D-Arabitol | − |
| L-Arabitol | − |
| Potassium gluconate | − |
| Potassium 2-ketogluconate | − |
| Potassium 5-ketogluconate | − |

Note:
"+" indicates that *Lactobacillus rhamnosus* strain LRH05 is capable of fermenting the carbohydrate tested to produce an acid, whereas "−" indicates that the strain has no such capability.
"/" indicates that the capability is undetermined.

The aforesaid result was subjected to comparison with the data in the APIWEB™ on-line bacteria and yeast PP1T, database, and it was found that the carbohydrate fermentation profile of *Lactobacillus rhamnosus* strain LRH05 of the present disclosure has 99.9% identity to that of *Lactobacillus rhamnosus*, suggesting that the *Lactobacillus rhamnosus* strain LRH05 characterized thus far by the applicant is different from conventionally known strains of *Lactobacillus rhamnosus*.

Based on the aforementioned characterization results, the applicant believes that the *Lactobacillus rhamnosus* strain LRH05 is a novel strain of *Lactobacillus rhamnosus*. As such, *Lactobacillus rhamnosus* strain LRH05 has been deposited at the Biosource Collection and Research Center (BCRC) of the Food Industry Research and Development Institute (FIRDI), Taiwan under an accession number BCRC 911013 since Jul. 31, 2020, and has also been deposited at the Deutsche Sammlung von Mikroorganismen und Zellkulturen (DSMZ) GmbH under an accession number DSM 33616 since Aug. 10, 2020 in accordance with the Budapest Treaty.

Example 3. Evaluation of the Effect of *Lactobacillus Rhamnosus* LRH05 on Alleviating Obesity-Related Metabolic Syndrome A. Preparation of Liquid Culture of Lactic Acid Bacterial (LAB) Strain A respective one of *Lactobacillus rhamnosus* LRH05 and *Lactobacillus* isolate LR47 (which was identified and designated as *Lactobacillus reuteri* LR47) was inoculated in a MRS broth, and was then cultivated in an incubator (37° C.) for 16 hours to obtain a respective culture. After centrifugation at 3,000 rpm and 4° C. for 10 minutes, the resultant cell pellet was collected, and was washed with phosphate-buffered saline (PBS), followed by suspending in PBS, so as to obtain a bacterial suspension having a bacterial concentration of 109 CFU/mL.

B. Induction of Obesity and Determination of Body Weight and Body Weight Gain

The C57BL/6 mice were divided into four groups, including a normal control group, a pathological control group, a comparative group, and an experimental group (n=8 per each group). The mice of the normal control group were fed with a low-fat diet containing 10 kcal fat (Research Diets, Inc., Cat. No. D12450B) and a 0.85% sodium chloride solution ad libitum. The mice of the pathological control group, comparative group, and experimental group were fed with a high-fat diet containing 60 kcal % fat (Research Diets, Inc., Cat. No. D12492) and a 0.85% sodium chloride solution ad libitum. Each mouse was fed for a total period of 10 weeks.

On the first day after feeding the fat-containing diet to the mice in each group, the mice of the experimental group were fed, via oral gavage, with 0.2 mL of the bacterial suspension of *Lactobacillus rhamnosus* LRH05 prepared in section A of this example, and the mice of the comparative group were fed, via oral gavage, with 0.2 mL of the bacterial suspension of *Lactobacillus reuteri* LR47 prepared in section A of this example. In addition, the mice of the normal control group and pathological control group were fed, via oral gavage, with 0.2 mL of a 0.85% sodium chloride solution. Each mouse was fed once daily for a total period of 10 weeks.

Prior to the feeding of the fat-containing diet and at the end of each week after starting the feeding of the fat-containing diet, the body weight of each mouse were determined. The body weight gain of each mouse was determined at the end of Week 10 after starting the feeding of the fat-containing diet.

The data thus obtained were analyzed according to the method described in section 1 of "General Procedures".

Figure 2:
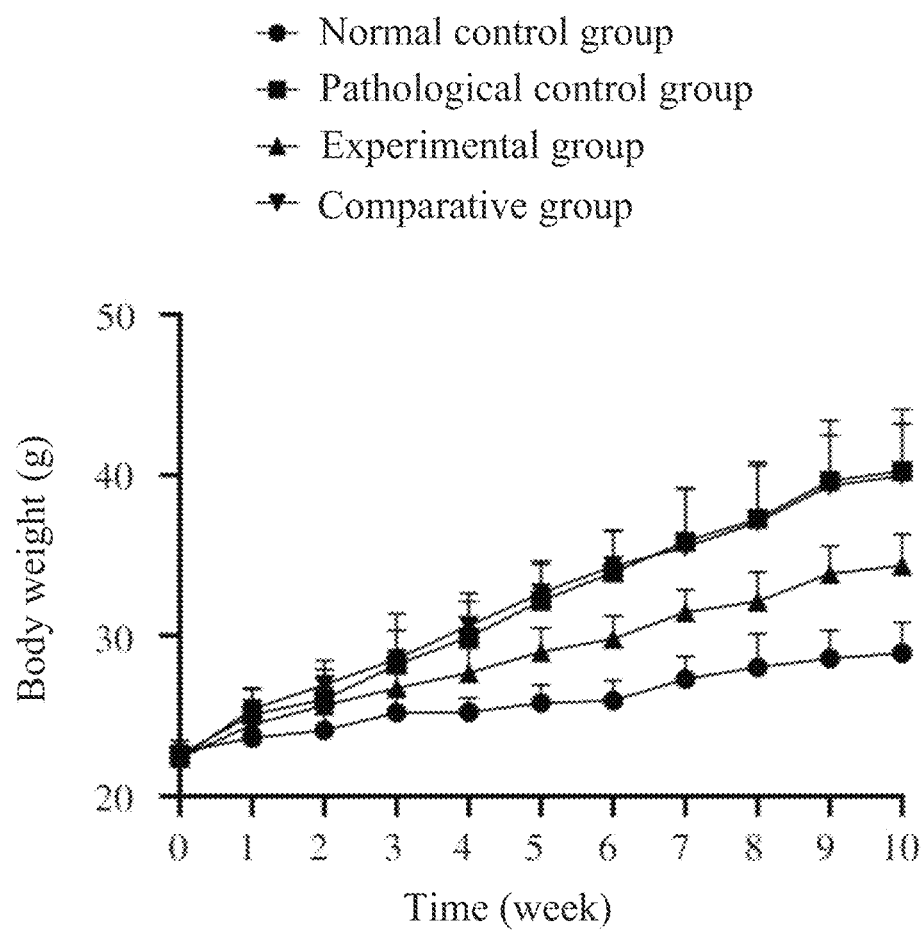
FIG. 2 shows the body weight of each group of Example 3, infra.
Figure 3:
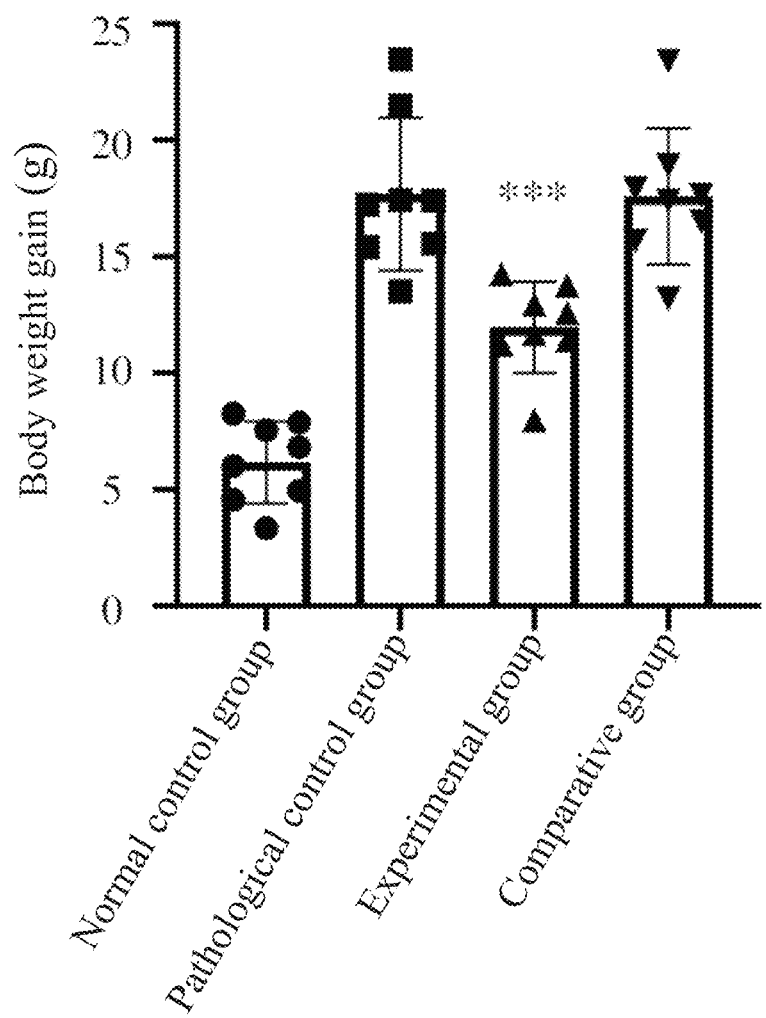
FIG. 3 shows the body weight gain of each group of Example 3, infra, in which the symbol "***" r $p<0.001$ (compared with the pathological control group)

Referring to FIGS. 2 and 3, in comparison with the normal control group, the body weight and body weight gain in each of the comparative group and pathological control group were greatly increased, while the body weight and body weight gain in the experimental group were only slightly increased, indicating that *Lactobacillus rhamnosus* LRH05 of the present disclosure can effectively alleviate obesity.

C. Preparation of Biological Samples

After completion of the determination of body weight and body weight gain at the end of Week 10 as described in section B of this example, the mice in each group were subjected to fasting for at least 12 hours overnight. Thereafter, all the mice were sacrificed by virtue of isoflurane, and the blood sample, fecal sample, epididymal white adipose tissue (WAT), retroperitoneal WAT, inguinal WAT, and liver tissue were obtained from each mouse carcass and were used for the following experiments.

D. Determination of Blood Glucose Level

The blood sample of each mouse obtained in section C of this example was subjected to centrifugation at 3,000 rpm and 4° C. for 10 minutes, so as to obtain a serum sample. The serum sample thus obtained was subjected to determination of blood glucose level using a Accu-Chek®, Performa blood glucose meter (Roche).

The data thus obtained were analyzed according to the method described in section 1 of "General Procedures".

Figure 4:
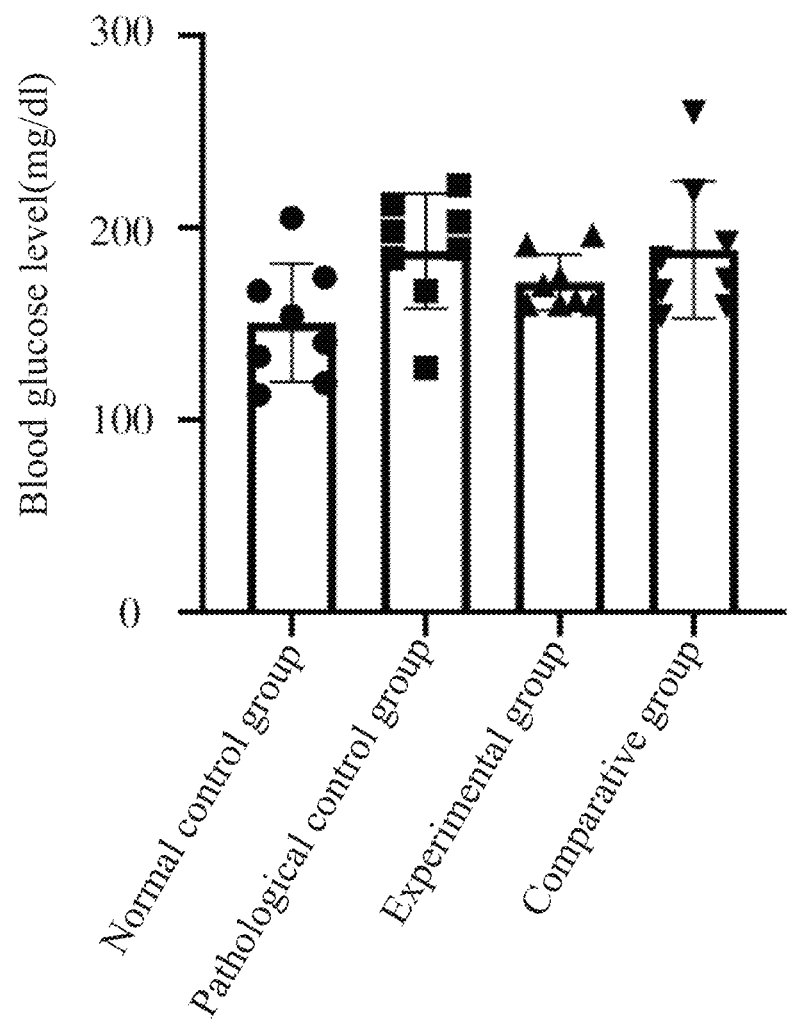
FIG. 4 shows the blood glucose level in each group of Example 3, infra.

Referring to FIG. 4, the blood glucose level determined in the experimental group was lower than those determined in the pathological control group and the comparative group, indicating that *Lactobacillus rhamnosus* LRH05 of the present disclosure is capable of controlling blood glucose levels.

E. Determination of Contents of TG and Total Cholesterol (TC) in Serum Sample

The serum sample of the respective mouse obtained in section D of this example was subjected to determination of the contents of TG and TC using a Cobas®800 modular analyzer (Roche).

The data thus obtained were analyzed according to the method described in section 1 of "General Procedures".

Figure 5:
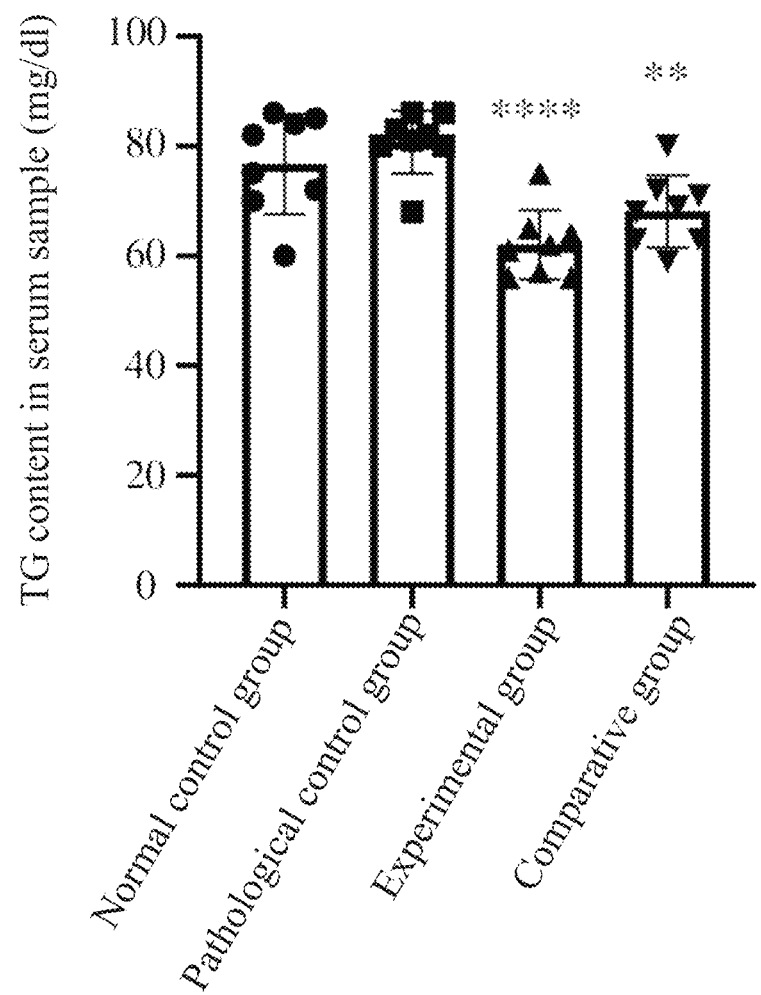
FIG. 5 shows the TG content in the serum of each group of Example 3, infra, in which the symbols "" and "**" respectively represent $p<0.1$ and $p<0.0001$ (compared with the pathological control group)
Figure 6:
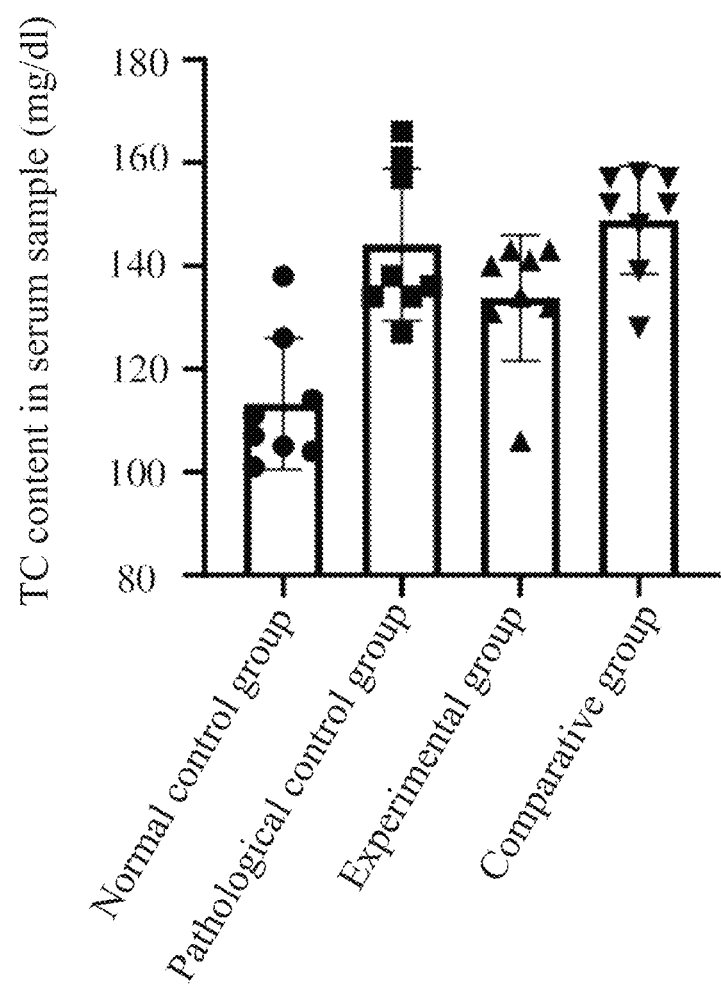
FIG. 6 shows the total cholesterol (TC) content in serum of each group of Example 3, infra.

Referring to FIGS. 5 and 6, the contents of TG and TC determined in the experimental group were lower than those determined in the pathological control group and the comparative group, indicating that *Lactobacillus rhamnosus* LRH05 of the present disclosure is capable of alleviating dyslipidemia.

F. Determination of Body Fat

The epididymal WAT, retroperitoneal WAT, and inguinal WAT of the respective mouse obtained in section C of this example were subjected to weight measurement.

The data thus obtained were analyzed according to the method described in section 1 of "General Procedures".

Figure 7:
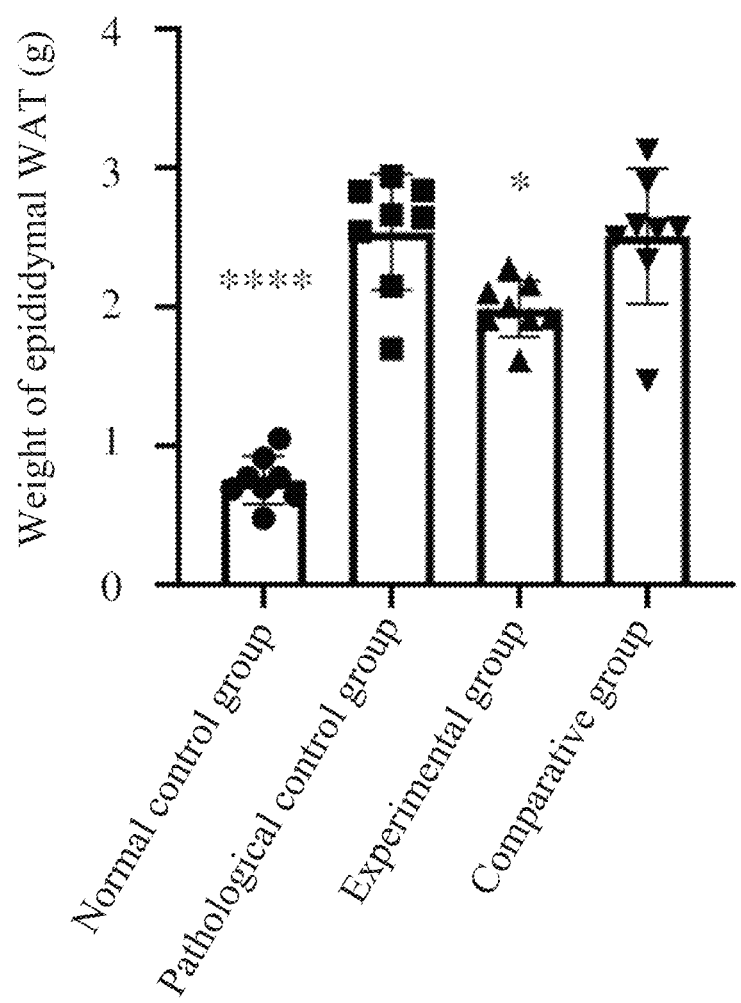
FIG. 7 shows the weight of the epididymal white adipose tissue (WAT) in each group of Example 3, infra, in which the symbols "*" and "****" respectively represent $p\leq0.05$ and $p\leq0.0601$ (compared with the pathological control group)
Figure 8:
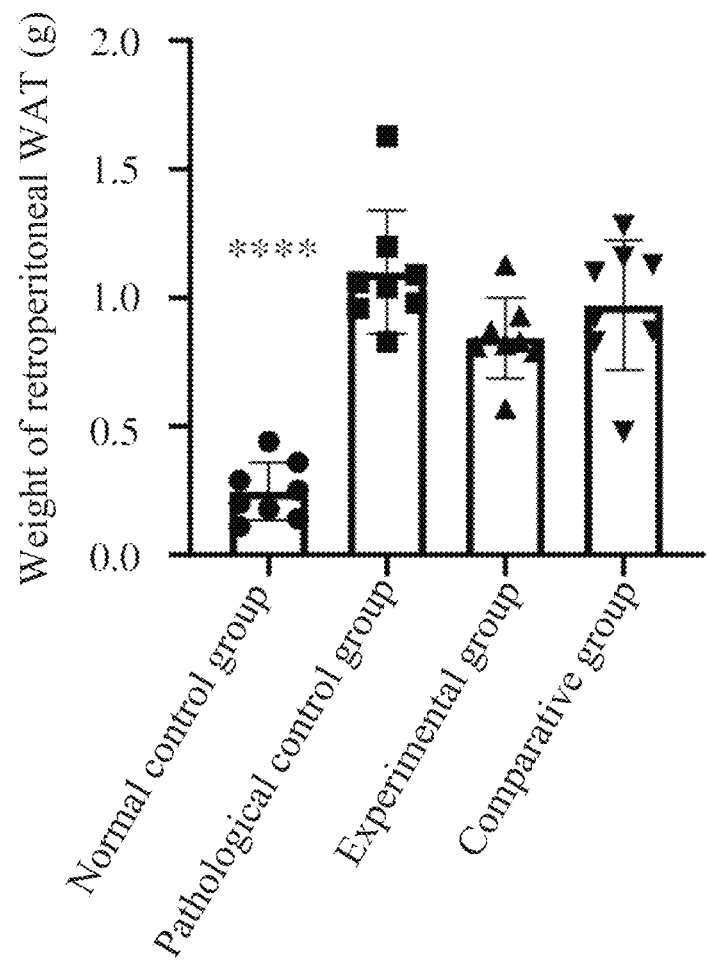
FIG. 8 shows the weight of the retroperitoneal WAT in each group of Example 3, infra, in which the symbol "****" represents $p<0.0001$ (compared with the pathological control group)
Figure 9:
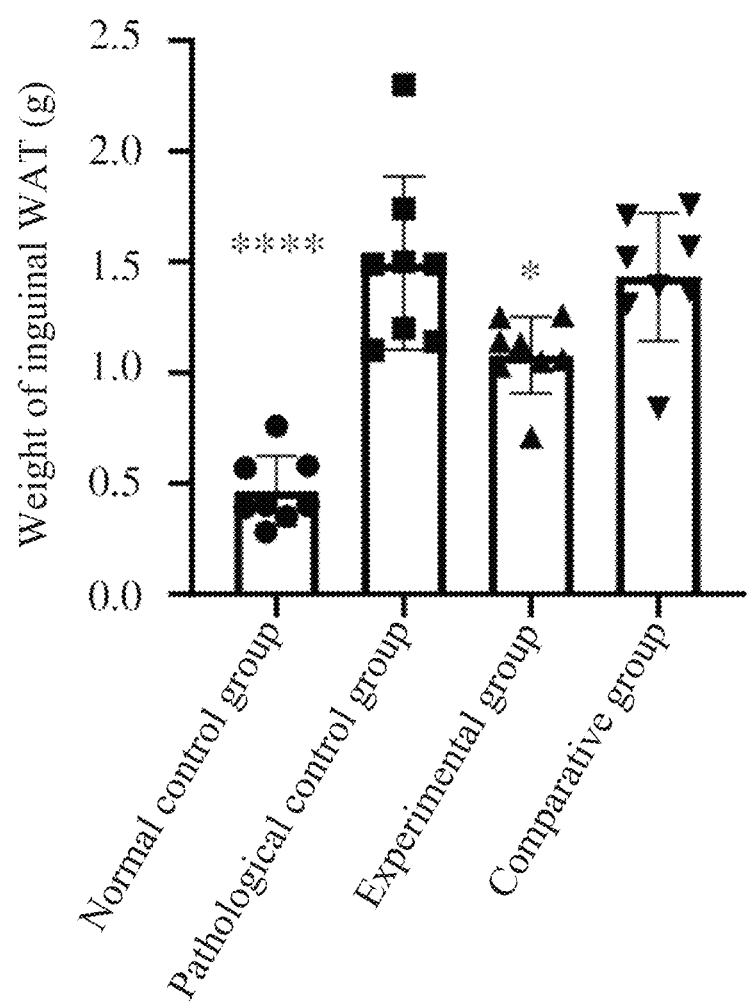
FIG. 9 shows the weight of the inguinal WAT in each group of Example 3, infra, in which the symbols "*" and "****" respectively represent $p<0.05$ and $p<0.0001$ (compared with the pathological control group)

Referring to FIGS. 7 to 9, the weights of the epididymal WAT, retroperitoneal WAT, and inguinal WAT determined in the experimental group were lower than those determined in the pathological control group and the comparative group, indicating that *Lactobacillus* rhainnosus LRH05 of the present disclosure can effectively reduce body fat.

G. Histopathologic Analysis and Determination of TG Content in Liver Tissue 0.2 g of the liver tissue of each mouse obtained in section C of this example was fixed with a 10% formaldehyde aqueous solution at room temperature for 24 hours, and the fixed tissue sample was then embedded with paraffin, followed by slicing to obtain a tissue section. The tissue section was stained using a hematoxylin and eosin (H&E) staining protocol well-known to those skilled in the art, and was observed under a Motic EasyScan Pro digital slide scanner (Motic Inc.) at 400× magnification.

In addition, 0.2 g of the respective one of the fixed tissue samples was subjected to determination of TG content using a triglyceride colorimetric assay kit (Cat. No. 10010303, Cayman, USA).

The data thus obtained were analyzed according to the method described in section 1 of "General Procedures".

Figure 10:
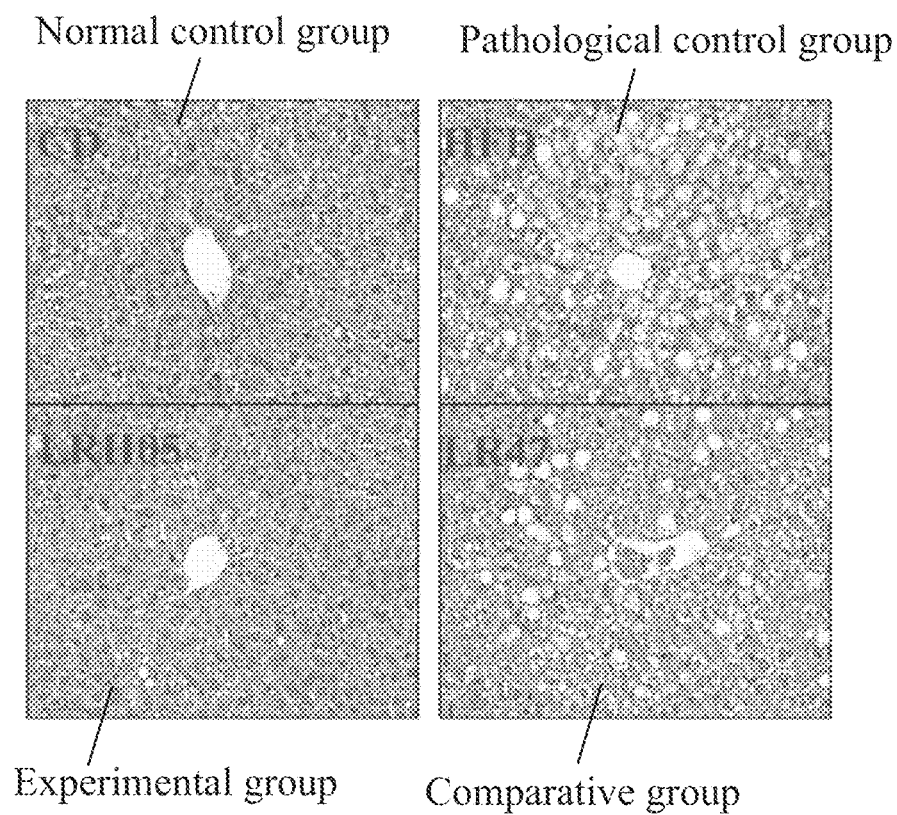
FIG. 10 shows the histological observation result of each group of Example 3, infra.

Referring to FIG. 10, in each of the pathological control group and the comparative group, severe fat accumulation was observed in the liver tissue. In contrast, in the experimental group, the liver tissue had a normal structure and no fat accumulation was observed therein.

Figure 11:
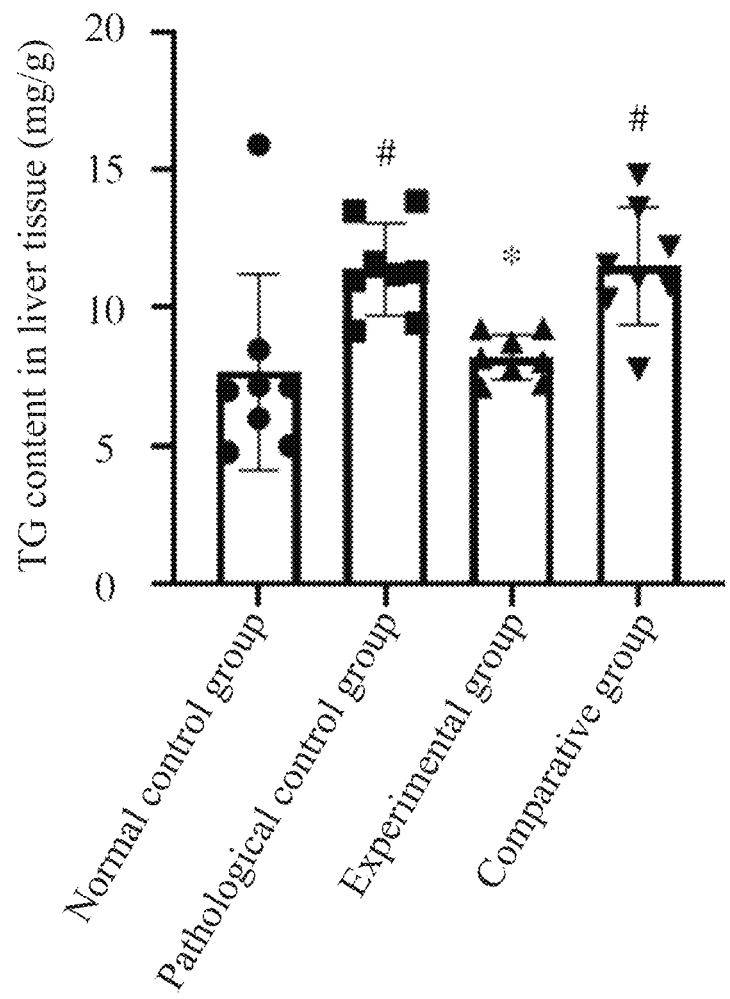
FIG. 11 shows the TG content in the liver tissue of each group of Example 3, infra, in which the symbol "#" represents $p<0.05$ (compared with the normal control group), and the symbol "*" represents $p<0.05$ (compared with the pathological control group)

Referring to FIG. 11, the liver TG content determined in the experimental group was lower than those determined in the pathological control group and the comparative group.

These results indicate that Lactobacillusrhamnosus LRH05 of the present disclosure can effectively reduce fat accumulation in liver tissues and ameliorate hepatic steatosis, and hence can alleviate fatty liver diseases (FLD).

Example 4. Evaluation of the Effect of Lactobacillus Rhamnosus LRH05 on Alleviating Diabetes Mellitus Experimental Procedures:

The in vitro α-amylase inhibitory activity was analyzed using a method slightly modified from that described by M. N. Wickramaratne et al. (2016), *BMC Complement. Altern. Med.*, 16(1):466. Briefly, 12 g of potassium sodium tartrate tetrahydrate was dissolved in 8 mL of a 2 M sodium hydroxide solution, followed by adding 20 mL of a 96 mM 3,5-dinitrosalicylic acid (DNSA) solution and 12 mL of ddH$_2$O, so as to obtain a DNSA reagent.

50 μL of the cell-free intracellular extract of *Lactobacillus rhamnosus* LRH05 (which was used as an experimental group) obtained in Example 1 was mixed with 50 μL of an α-amylase solution (5 U/mL) (Sigma-Aldrich), followed by being left standing for reaction to proceed at 30° C. for 10 minutes. Thereafter, 50 μL of a starch solution (1% (w/v), in PBS) was added into the resultant mixture, followed by being left standing for reaction to proceed at 30° C. for 3 minutes. Subsequently, 50 μL of the DNSA reagent was added into the resultant mixture, followed by heating in a 90° C. water bath for 10 minutes. Thereafter, the reaction mixture thus obtained was allowed to cool to room temperature, followed by adding 1 mL of ddH$_2$O. The resultant reaction mixture was subsequently subjected to determination of absorbance at a wavelength of 540 nm (OD$_{540}$) by a spectrophotometer (TECAN, SUNRISE).

In addition, a cell-free intracellular extract of *Lactobacillus rhamnosus* GG (LGG) was prepared according to the method described in section B of Example 1, and was used as a comparative group. 30 mg/mL of acarbose (in ddH$_2$O) was used as a positive control group, and a 0.853 (w/v) sodium chloride solution was used as a control group. The comparative group, positive control group, and control group were subjected to the same experiment described above.

The α-amylase inhibition rate (K) was calculated using the following Equation (I):

$$A = [(B-C)/B] \times 100 \quad (I)$$

where A=α-amylase inhibition rate (%)
B=OD$_{540}$ value of the control group
C=OD$_{540}$ value of the respective one of the experimental group, comparative group, and positive control group The data thus obtained were analyzed according to the method described in section 1 of "General Procedures".

Figure 12:
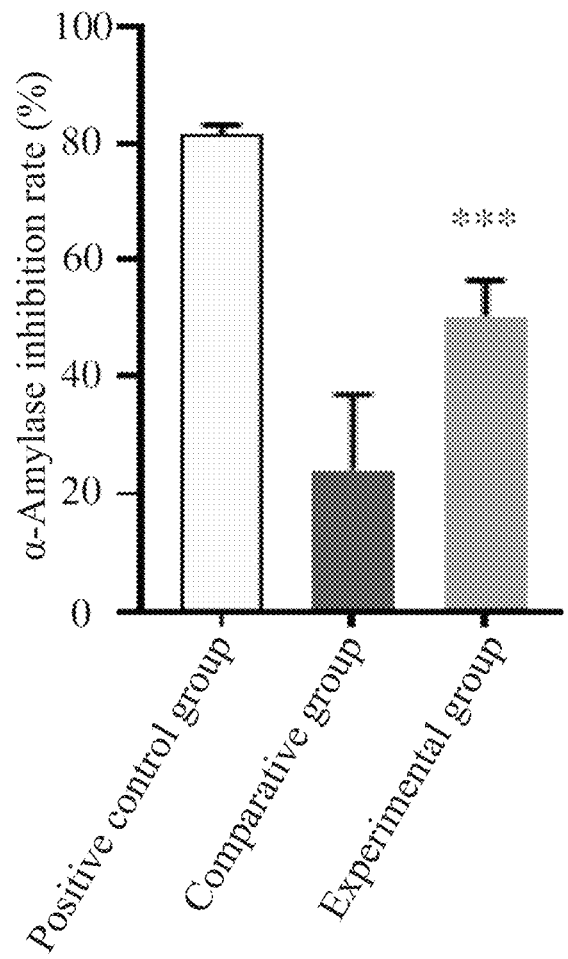
FIG. 12 shows the α-amylase inhibition rate of each group of Example 4, infra, in which the symbol "***" represents $p<0.001$ (compared with the comparative group)

Results:

Referring to FIG. 12, the α-amylase inhibition rate determined in the experimental group was higher than that determined in the comparative group, indicating that *Lactobacillus rhamnosus* LRH05 of the present disclosure is capable of treating and/or alleviating diabetes mellitus.

Example 5. Evaluation of the Effect of Lactobacillus Rhamnosus LRH05 on Modifying Gut Microbiota A. Analysis of Gut Microbiota Composition The fecal samples (n=6) of each group obtained in section C of Example 3 were subjected to analysis of gut microbiota composition using a method slightly modified from that described by X. P. Li et al. (2020), *J. Funct. Foods*, 73:104103. Briefly, the gut microbiota DNA in the respective fecal sample was extracted using a QIAamp DNA Stool Mini Kit (Cat. No. 51604, QIAGEN, Germany) in accordance with the manufacturer's instructions.

The thus obtained gut microbiota DNA was used as a template and was subjected to polymerase chain reaction (PCR) that was performed using a primer pair (i.e., forward primer F and reverse primer R) having the following nucleotide sequence and designed for a 16S rDNA sequence.

Forward primer F
5'-tcgtcggcagcgtcagatgtgtataagagacagcctacgggnggcwgc ag-3' (SEQ ID No: 4)
Reverse primer R
5'-gtctcgtgggctcggagatgtgtataagagacaggactachvgggtat ctaatcc-3' (SEQ ID No: 5)

Thereafter, sequencing of the PCR product was performed using Illumina MiSeq sequencing system (Illumina, Inc., USA). The 16S rDNA sequence thus obtained was subjected to sequencing analysis using QIIME microbiome bioinformatics platform (version 1.9.1, QIIME), and was classified through operational taxonomic units (OTUs) using USEARCH (version 7.0.1090). Thereafter, 16S rDNA sequence alignment was conducted using Ribosomal Database Project (RDP) Classifier (Michigan State University, USA) and Python Nearest Alignment Space Termination (PyNAST) (version 1.2) in accordance with the data in the Greengenes database (version gg_13_8), SILVA database (version 132), or NCBI's gene database.

Species richness indexes (i.e., Chao1 and abundance-based coverage estimator (ACE)) were analyzed using QIIME microbiome bioinformatics platform, followed by estimating α-diversity of gut microbiota in each group.

Figure 13:
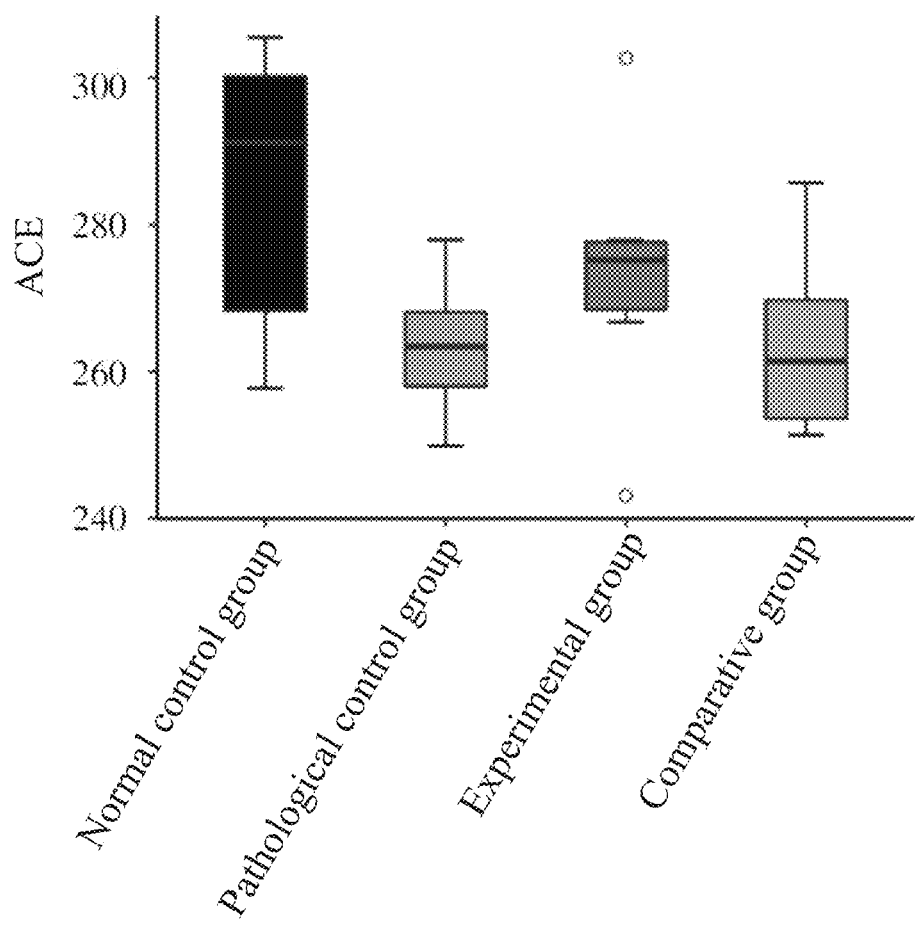
FIG. 13 shows the abundance-based coverage estimator (ACE) of each group of Example 5, infra.
Figure 14:
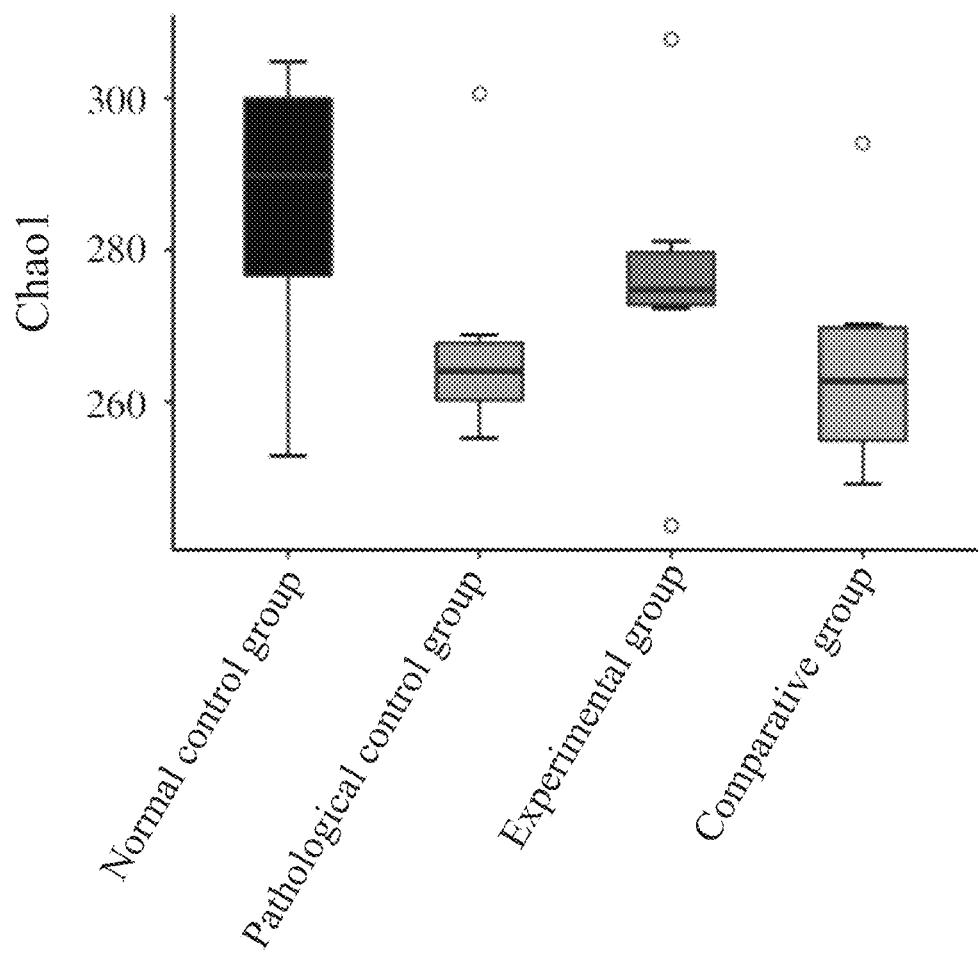
FIG. 14 shows the Chao1 of each group of Example 5, infra.

Referring to FIGS. 13 and 14, Chao1 and ACE determined in the experimental group were higher than those determined in the comparative group and the pathological control group, indicating that *Lactobacillus rhamnosus* LRH05 of the present disclosure can effectively improve the balance of normal gastrointestinal microflora.

B. Analysis of Short-Chain Fatty Acids

The fecal samples of each group obtained in section C of Example 3 were subjected to analysis of short-chain fatty acids using a method slightly modified from that described by T. Torii et al. (2010), *Ann. Clin. Biochem.*, 47 (Pt 5):447-452. Briefly, 70 mg of the respective fecal sample was mixed with 700 μL of a 70% (v/v) ethanol solution, and a suitable amount of glass beads (size: 0.1 mm) was then added to the resultant mixture, followed by shaking for 10 minutes. After centrifugation at 12,000 rpm and 4° C. for 10 minutes, the resultant supernatant was collected, and was subjected to the following derivatization process. 0.3 mL of the respective supernatant was mixed with 0.05 mL of 2-ethylbutyric acid (serving as an internal standard) (Sigma-Aldrich, Cat. No. 109959), 0.3 mL of 3% pyridine (Sigma-Aldrich, Cat. No. 270970), 0.3 mL of 250 mmol/L 1-ethyl-3-(3-dimethylaminopropyl) carbodiimide hydrochloride (EDC-HCl) (Sigma-Aldrich, Cat. No. 03449), and 0.3 mL of 20 mmol/L 2-nitrophenylhydrazine hydrochloride (NPH—HCl) (Tokyo Chemical Industry Co., Ltd., Cat. No. N0231), followed by being left standing for reaction to proceed at 60° C. for 20 minutes. Subsequently, 0.2 mL of a reagent (prepared from a 15% (w/v) potassium hydroxide solution and methanol in a ratio of 80:20 (v/v)) was added to the resultant mixture to terminate the reaction.

Thereafter, the reaction mixture thus obtained was allowed to cool to room temperature, followed by adding 3 mL of a 0.5 mol/L phosphoric acid solution and 4 mL of ether. After shaking for 3 minutes, the resultant ether layer was collected, and was mixed with 4 mL of ddH$_2$O, followed by shaking for 3 minutes. After centrifugation at 3,000 rpm and 4° C. for 10 minutes, the resultant ether layer was collected, and ether was eliminated using nitrogen gas. The fatty acid hydrazide thus obtained was dissolved in a suitable amount of methanol to obtain a test sample, and then high performance liquid chromatography (HPLC) analysis was conducted, so as to determine the contents of short-chain fatty acids therein.

HPLC analysis was performed using an HPLC system (HITACHI L-7300) equipped with a HITACHI L-7420 UV-VIS detector and the operating conditions shown in Table 4 below.

TABLE 4

| | |
|---|---|
| Type of Column | MN NUCLEODUR ® C18 HTec |
| Column temperature | 40° C. |
| Mobile phase | Methanol/ddH$_2$O (16:84, v/v) |
| Flow rate | 1.0 mL/min |
| Sample injection volume | 20 μL |
| Detection wavelength | 400 nm |

In addition, acetic acid, propionic acid, and butyric acid were used as standard specimens (which were purchased from Sigma-Aldrich and each of which was provided at concentrations of 1.25, 2.5, 5, 10, and 20 mmol/L, and were subjected to the same derivatization process and HPLC analysis.

The data thus obtained were analyzed according to the method described in section 1 of "General Procedures".

Figure 15:
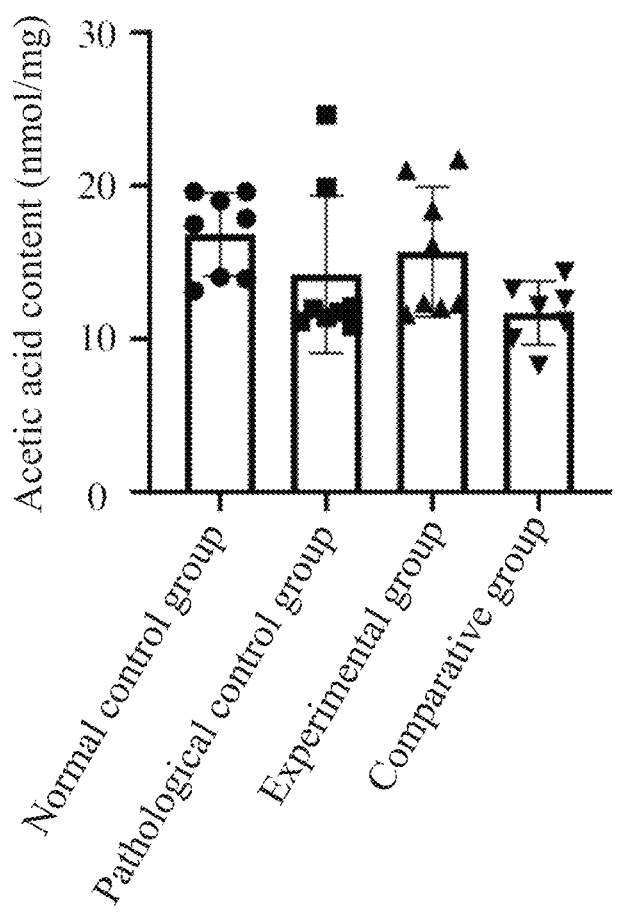
FIG. 15 shows the acetic acid content in each group of Example 5, infra.
Figure 16:
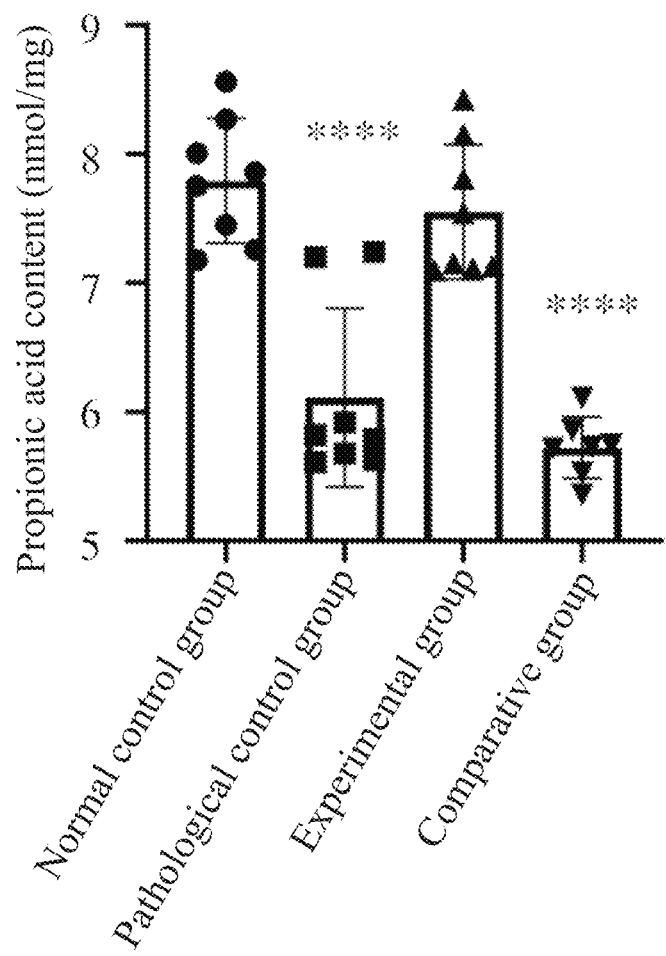
FIG. 16 shows the propionic acid content in each group of Example 5, infra, in which the symbol "**" represents $p<0.0001$ (compared with the normal control group)
Figure 17:
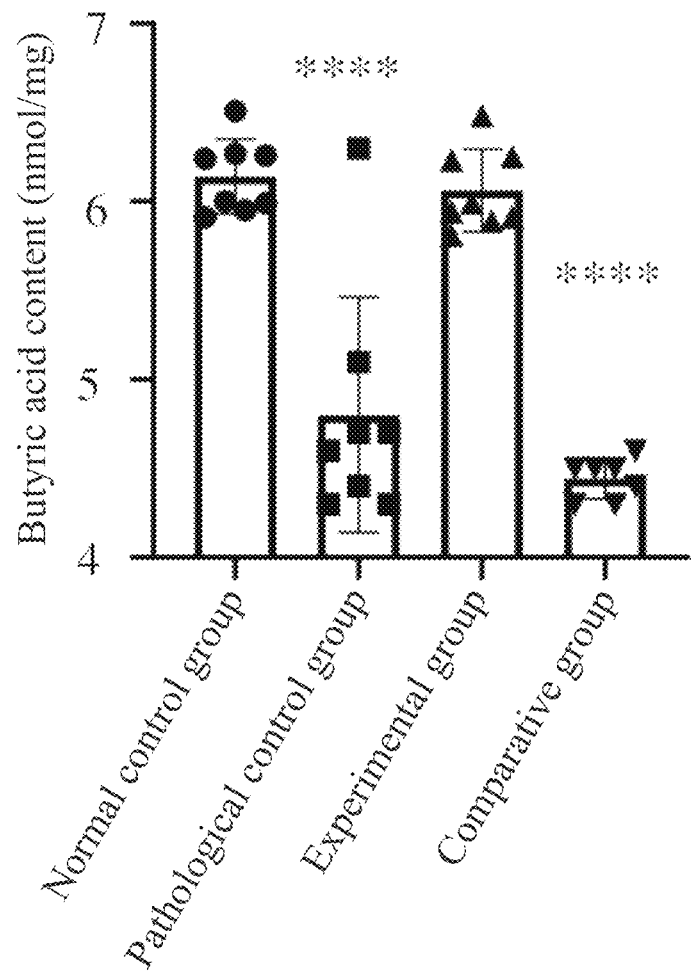
FIG. 17 shows the butyric acid content in each group of Example 5, infra, in which the symbol "**" represents $p<0.0001$ (compared with the normal control group).

Referring to FIGS. 15 to 17, the contents of acetic acid, propionic acid, and butyric acid determined in the experimental group were higher than those determined in the comparative group and the pathological control group, indicating that *Lactobacillus rhamnosus* LRH05 of the present disclosure can effectively improve the consumption of dietary fibers, proteins, and peptides by gut microbiota, and hence can provide positive metabolic effects.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed:

1. A method for treating diabetes mellitus, comprising administering to a subject in need thereof a pharmaceutical composition containing an isolated strain of *Lactobacillus rhamnosus* LRH05, wherein the isolated strain of *Lactobacillus rhamnosus* LRH05 is deposited at Deutsche Sammlung von Mikroorganismen und Zellkulturen GmbH under an accession number DSM 33616.

2. The method of claim 1, wherein the pharmaceutical composition is in a dosage form for oral administration.

3. The method of claim 1, wherein the diabetes mellitus is type 2 diabetes mellitus (T2DM).

* * * * *